United States Patent [19]

Stark

[11] Patent Number: 5,433,197
[45] Date of Patent: Jul. 18, 1995

[54] NON-INVASIVE GLUCOSE MEASUREMENT METHOD AND APPARATUS

[76] Inventor: Edward W. Stark, 160 W. End Ave., Suite 3M, New York, N.Y. 10023

[21] Appl. No.: 940,691
[22] Filed: Sep. 4, 1992
[51] Int. Cl.⁶ ............................................. A61B 5/00
[52] U.S. Cl. ..................................... 128/633; 128/664
[58] Field of Search ................................ 128/633–634, 128/664–667; 356/39–41

[56] References Cited

U.S. PATENT DOCUMENTS

| | | |
|---|---|---|
| 3,638,640 | 2/1972 | Shaw . |
| 3,958,560 | 5/1976 | March . |
| 3,963,019 | 6/1976 | Quandt ............................ 128/633 |
| 4,014,321 | 3/1977 | March . |
| 4,017,192 | 4/1977 | Rosenthal . |
| 4,167,331 | 9/1979 | Nielsen . |
| 4,169,976 | 10/1979 | Kaiser . |
| 4,223,680 | 9/1980 | Jöbsis . |
| 4,305,398 | 12/1981 | Sawa ............................... 128/633 |
| 4,427,889 | 1/1984 | Muller . |
| 4,570,638 | 2/1986 | Stoddart . |
| 4,655,225 | 4/1987 | Dahne et al. ..................... 128/633 |
| 4,725,147 | 2/1988 | Stoddart . |
| 4,817,623 | 4/1989 | Stoddart . |
| 4,863,265 | 9/1989 | Flower . |
| 4,975,581 | 12/1990 | Robinson . |
| 4,997,281 | 3/1991 | Stark . |
| 5,028,787 | 7/1991 | Rosenthal . |
| 5,070,874 | 12/1991 | Barnes et al. .................... 128/633 |
| 5,077,476 | 12/1991 | Rosenthal ..................... 128/633 X |
| 5,086,229 | 2/1992 | Rosenthal et al. ............. 128/633 X |
| 5,204,532 | 4/1993 | Rosenthal ..................... 128/633 X |
| 5,209,231 | 5/1993 | Cote et al. ....................... 128/633 |
| 5,219,400 | 6/1993 | Jacot et al. ................... 128/664 X |
| 5,243,933 | 9/1993 | Tarr et al. ........................ 128/633 |
| 5,318,022 | 6/1994 | Taboada et al. .............. 128/664 X |

FOREIGN PATENT DOCUMENTS

0160768 11/1985 European Pat. Off. .
WO93/07801 4/1993 WIPO .

OTHER PUBLICATIONS

Reim M. et al., "Steady state levels of glucose in the different layers of the cornea, aqueous humor, . . . ", Ophthalmologica 154 39–50 (1967).
Rabinovitch B. et al., "Non-invasive glucose monitoring of the aqueous humor of the eye: Part I Measurement . . . " Diabetes Care 5(3):254–258 1982.

(List continued on next page.)

*Primary Examiner*—Angela D. Sykes
*Attorney, Agent, or Firm*—McAulay, Fisher, Nissen, Goldberg & Kiel

[57] ABSTRACT

A glucose sensor to provide a non-invasive means of determining blood glucose which is of particular value in the diagnosis and treatment of diabetes. The patient's eye is illuminated with near-infrared radiation which passes into the eye through the cornea and the aqueous humor, is reflected from the iris and/or lens surface, and then passes out through the aqueous humor and cornea. The reflected radiation is collected and detected by a near-infrared sensor which measures the reflected energy in one or more wavelength bands. Comparison of the reflected energy with the source energy provides a measure of the spectral absorption by the eye which is characteristic of the composition of the cornea, the aqueous humor, and the other structures within the eye through which the energy is transmitted or from which it is reflected. In particular, the level of glucose in the aqueous humor is a function of the level of glucose in the blood so that non-invasive determinations of blood glucose may be obtained by suitable calibration relating the measured spectral absorption of the aqueous humor to the measured blood glucose level. To obtain specificity and accuracy, the spectral data at several or many wavelengths may be utilized with a multivariate calibration and prediction process to separate the glucose information from the spectral influences of interfering substances, such as water, which also absorb the near-infrared radiation within the wavelength region utilized for the measurement. The system includes a computer for processing the spectral data and a display for readout of the result.

30 Claims, 7 Drawing Sheets

OTHER PUBLICATIONS

March W. F. et al., "Non-invasive glucose monitoring of the aqueous humor of the eye: Part II. Animal studies . . . " Diabetes Care 5 (3): 259–265 (1982).

Schrady N., "The view from a distance; advances in optics and electronics are allowing physicians to glean . . . ", Forbes 135 (2): 142 (1985).

Chance B. et al., "Comparison of time-resolved and unresolved measurements of deoxyhemoglobin in brain", Proc. Natl. Acad. Sci. USA 85: 4971–4975.

Ferrari M. e al., "Continuous non-invasive monitoring of human brain by near-infrared spectroscopy", Adv Exp Med Biol 191:873–882 (1985).

Seiyama A. et al., "Simultaneous Measurement of Haemoglobin oxygenation of brain and skeletal muscle . . . ", Adv Exp Med Biol 215: 291–295 (1987).

Hazeki O. et al. "Near-infrared spectrophotometric monitoring of haemoglobin and cytochrame $a, a_4$ in situ", Adv Exp Med Biol 215: 283–289 (1987).

Tamura M. et al., "Spectroscopic characteristics of rat skeletal and cardiac tissues in the visible and . . . ", Adv Exp Med 215: 297–300 (1987).

Takada M. et al., "Non-invasive near-infrared measurements of human arm tissues in vivo", Adv Exp Med Biol 215: 301–304 (1987).

Heise H., R. Marbach, et al., "Multivariate determination of blood . . . " Institute fur Spektrochemie und angewandte Spektroskopie, D–4600 Dortmund 1.

Ferrari M. et al., "Determination of cerebral venous hemoglobin saturation by derivative near infrared spectroscopy", Adv Exp med Biol 248:47–53 (1989).

Martens H. and T. Naes, "Multivariate Calibration", John Wiley and Sons, New York (1989) ISBN 0 471 90979 3.

NON-INVASIVE GLUCOSE MEASUREMENT METHOD AND APPARATUS

BACKGROUND OF THE INVENTION a) Field of the Invention

The present invention relates to instruments and methods for the spectrophotometric determination of glucose in the aqueous humor of the eye and the estimation of the level of glucose in the blood based on the values thus obtained.

b) Background Art

An important aspect in the treatment of diabetes is the frequent determination of the blood glucose level of the patient so as to manage food intake and the dosage and timing of insulin injections. Presently, blood glucose analyzers for home use by the patient require lancing of the finger to obtain a drop of blood. The blood is placed on a strip containing reagents which react with glucose to form a chromophor which is then read by a reflectance colorimeter within the analyzer. This procedure is painful and it may result in infections which are particularly hazardous to diabetic persons. In addition, the annual cost of reagent strips can range from several hundred to over one thousand dollars per year per patient.

Non-invasive in vivo determination of blood constituents by near-infrared spectroscopy was first applied to oximetry, the determination of the oxygen content of the blood based on the spectral characteristics of hemoglobin and oxyhemoglobin. Wood (U.S. Pat No. 2,706,927) described a method using two wavelengths of light. Shaw (U.S. Pat. No. 3,638,640) improved this procedure by using more wavelengths of light. This technique was made significantly more practical by use of the modulation caused by the pulse as invented in 1972 by Aoyagi (Japanese Application 947714, April 1979). Improvements were described by Nielsen (U.S. Pat No. 4,167,331) and Flower (U.S. Pat. No. 4,863,265). This pulse oximetry technique is in routine clinical use. Jöbsis (U.S. Pat. No. 4,223,680), Chance, Ferrari, Hazeki, Seiyama, Tamura, Takada and co-workers have applied spectrophotometric techniques to the in vivo determination of oxygen in the brain and other tissues. Research in this area continues. Relevant publications include: Chance Bet al., "Comparison of time-resolved and -unresolved measurements of deoxyhemoglobin in brain", Proc. Natl. Acad. Sci. USA 85: 4971–4975; Ferrari M et al., "Continuous non-invasive monitoring of human brain by near-infrared spectroscopy", Adv Exp Med Biol 191:873–882 (1985); Hazeki O et al., "Near-infrared spectrophotometric monitoring of haemoglobin and cytochrome a,$a_3$ in situ" Adv Exp Med Biol 215: 283–289 (1987); Seiyama A et al., "Simultaneous Measurement of Haemoglobin oxygenation of brain and skeletal muscle of rat in vivo by near-infrared spectrophotometry", Adv Exp Med Biol 215: 291–295 (1987); Tamura M et al., "Spectroscopic characteristics of rat skeletal and cardiac tissues in the visible and near-infrared region", Adv Exp Med Biol 215:297–300 (1987); Takada M et al., "Non-invasive near-infrared measurements of human arm tissues in vivo", Adv Exp Med Biol 215:301–304 (1987); Ferrari M et al., "Determination of cerebral venous hemoglobin saturation by derivative near-infrared spectroscopy" Adv Exp Med Biol 248:47–53 (1989).

Various workers have attempted to use near-infrared spectroscopy for the in vitro or in vivo characterization of tissue for malignancy including Rosenthal (U.S. Pat No. 4,017,192), who suggested in vitro examination, and Stoddart (U.S. Pat. Nos. 4,570,638, 4,725,147, and 4,817,623), who described an in vivo method and apparatus. To date these methods do not appear generally useful.

The use of in vivo spectrophotometric measurements for the non-invasive transcutaneous determination of glucose was described by Dähne and Cross (U.S. Pat. No. 4,655,225) using typically two wavelengths of near-infrared light in the range from 1000 to 2700 nanometers. Investigations by Peura and Mendelson were reported by Schrady in February 1985. Schrady N, "The view from a distance; advances in optics and electronics are allowing physicians to glean diagnostic information without drawing blood", Forbes 135 (2): 142 (1985). Schmidtke (DE 3541165, EP 226822) described a three-wavelength device for measurement of glucose through the ear lobe using interference filters at 805, 1300, and 1600 nanometer wavelengths and optical modulation at different frequencies to separate the information. Rosenthal (U.S. Pat. No. 5,028,787) describes a system for in vivo measurement of glucose in blood using transmission or interaction at least one pair of wavelengths in the spectral region between 600 and 1100 nanometers. Robinson (U.S. Pat. No. 4,975,581) describes methods and apparatus means for the determination of an analyte in biological fluid samples characterized by the algorithm and mathematical calibration model used to calculate unknown concentrations of the analyte. NASA has supported SBIR Phase 1 and Phase 2 programs in "Non-invasive blood analysis during manned space flight" under contract 90-1-12.02-1545 with Boston Advanced Technologies. To date, while the results are promising, none of these approaches has reached the level of precision and accuracy necessary for effective monitoring of blood glucose levels in vivo, largely due to the interferences from other blood constituents, notably hemoglobin in the 600 to 1100 nanometer region, and from various tissue components. In addition, the pulse and movements by the patient during measurement add temporal variations to the measurements.

March (U.S. Pat. Nos. 3,958,560 and 4,014,321) suggested the measurement of optical rotation to determine the glucose concentration in the aqueous humor of the eye which was then related to the blood glucose level of the patient. However, miniaturization and attachment of the measurement device to the eye in similar fashion to a contact lens proved impractical. However, Reim and March provide evidence that the glucose level in the aqueous humor is related to that in the blood and the lag time between blood glucose changes and aqueous humor concentrations is sufficiently short to allow monitoring of blood glucose via measurements on aqueous humor.

It is, accordingly, an object of the present invention to provide a new and improved apparatus for and method of using near-infrared energy for the determination of glucose concentration in the blood based on measurements made of the aqueous humor of the eye.

SUMMARY OF THE INVENTION

In accordance with one aspect of the present invention, a broad band of near-infrared energy is caused to illuminate the eye, particularly the corneal region, in such a manner that the energy passes through the aqueous humor in the anterior chamber of the eye and is then reflected from the iris. The reflected energy then passes back through the aqueous humor and the cornea and is collected for spectral analysis and detection. The constituents of the cornea, aqueous humor, and iris absorb near-infrared energy at different wavelengths in amounts that are characteristic of the materials and their concentration within the optical path. The electrical signals representative of the reflected optical energy at a multitude of wavelengths are processed using multivariate modeling and calibration techniques to provide for calculation and readout of the estimated blood glucose levels based on the spectral absorption of glucose and of the other interfering substances in the eye and the correlation of the spectral absorption within the eye to blood glucose levels.

Another implementation of the present invention provides that the eye is illuminated by a narrow wavelength band of energy, the center wavelength of which is sequentially varied continuously or in a stepwise manner so that a non-wavelength-specific detection means can provide electrical signals representative of the multitude of wavelengths necessary for determination of glucose as described above.

Yet another implementation of the present invention provides that a broad band of near-infrared energy is spectrally encoded, by means such as an interferometer, a time-variable encoding mask placed in a dispersed spectral image, an acousto-optical filter, the electrical modulation of multiple discrete sources, or other similar techniques known to the art. The multiplicity of encoded narrow wavelength bands are simultaneously used to illuminate the eye. The combined reflected energy is collected and converted to a composite electrical signal representative of the energy at all wavelengths simultaneously. This electrical signal is decoded by means such as the Fourier transform, Hadamard transform, or other techniques related to the original encodement technique to provide information relating to the reflected energy at each of the multiplicity of narrow wavelength bands which comprise the broad band illumination of the eye. These spectral data are used as above to determine blood glucose.

In accordance with another aspect of the present invention, the illumination and detection means are configured and positioned so that the specular reflection of the illumination from the curved anterior surface of the cornea is directed away from the detection means thereby preventing the spectroscopic errors associated with the detection of light which has not undergone absorption by the sample. In addition, the detection means is configured and positioned so that extraneous light from the surrounding environment is substantially blocked so that it does not reach the detection means.

In accordance with another aspect of the present invention, the illuminating energy is modulated optically or electrically and the detection and electrical signal processing means are made responsive only to said modulated signals while discriminating against signals that are unmodulated or those modulated at the frequency of the power line and its harmonics, thereby rejecting constant extraneous illumination such as sunlight and artificial sources which have a constant intensity and/or an intensity component which varies in accordance with the powerline frequency supplying said sources.

In accordance with another aspect of the present invention, the fixation means produce visible light so directed as to provide a fixation point for the user, thereby aiding the user to maintain the proper location and orientation of the apparatus. The intensity of this source is such that it will cause the pupil to contract thereby maximizing the reflecting area of the iris. Additional visual cues for the positioning of the device are provided by incorporation of more visible light sources in a pattern indicative of positioning errors and their direction, the light from which is all or partially blocked by the iris when the unit is correctly positioned. Additional visual indications are provided by blinking the light source at various rates or the use of additional sources arranged in accordance with the principles of this aspect of the invention.

In accordance with another aspect of the present invention, the electrical signals representative of the reflected energy are analyzed by univariate and/or multivariate signal processing techniques to determine whether the user has moved the apparatus, blinked, moved the eye, or otherwise caused changes in the measurement geometry that could cause errors in the glucose determination. The signals are also analyzed to ensure that they conform to the multivariate calibration model. The entire measurement sequence is repeated at a sufficiently high rate so that moderate motions typical of hand-held operation will not cause significant errors. Non-conforming signals are automatically rejected and not included in the signal averaging process. A visual and/or aural indication is provided for the user to indicate that the signals are suitable for processing thereby aiding correct operation by rapid feedback and reinforcement. When sufficient acceptable signals have been accumulated, the glucose value is computed and a different visual and/or aural signal is provided to notify the user that the measurement is complete.

For a better understanding of the present invention, reference is made to the following description and accompanying drawings while the scope of the invention will be pointed out in the appended claims.

DETAILED DESCRIPTION OF THE PREFERRED EMBODIMENTS AND BEST MODE

The invention uses the principle of passing light through a sample beyond which diffuse reflection takes place causing the light to return back through the sample for measurement, a technique that is sometimes called transflection. In the present invention, the sample comprises the cornea and aqueous humor of an eye while the diffuse reflector is the iris. Using the principles of multivariate modeling and calibration described by Martens and Naes (Martens H and T Naes, "Multivariate Calibration" John Wiley and Sons, New York (1989) ISBN 0 471 90979 3), the measured spectra are related to the blood glucose level of the person on whom the eye measurements were made. This relationship depends on the correlation between the glucose level in the aqueous humor of the eye and that of the blood which has been reported by Reim, March and others (Reim Met al., "Steady state levels of glucose in the different layers of the cornea, aqueous humor, blood and tears in vivo", Ophthalmologica 154: 39–50 (1967); March WF et al., "Non-invasive glucose monitoring of the aqueous humor of the eye: Part II Animal studies and the scleral lens" Diabetes Care 5 (3): 259–265 (1982)). Because of this correlation, it is not necessary to directly measure the glucose concentration in the aqueous humor in order to generate the multivariate model and calibration but rather, the calibration modeling may be performed using the blood glucose level in relationship to the measured spectral data. In addition, the iris, which is supplied with blood, will contribute to the measured spectra.

Figure 1:
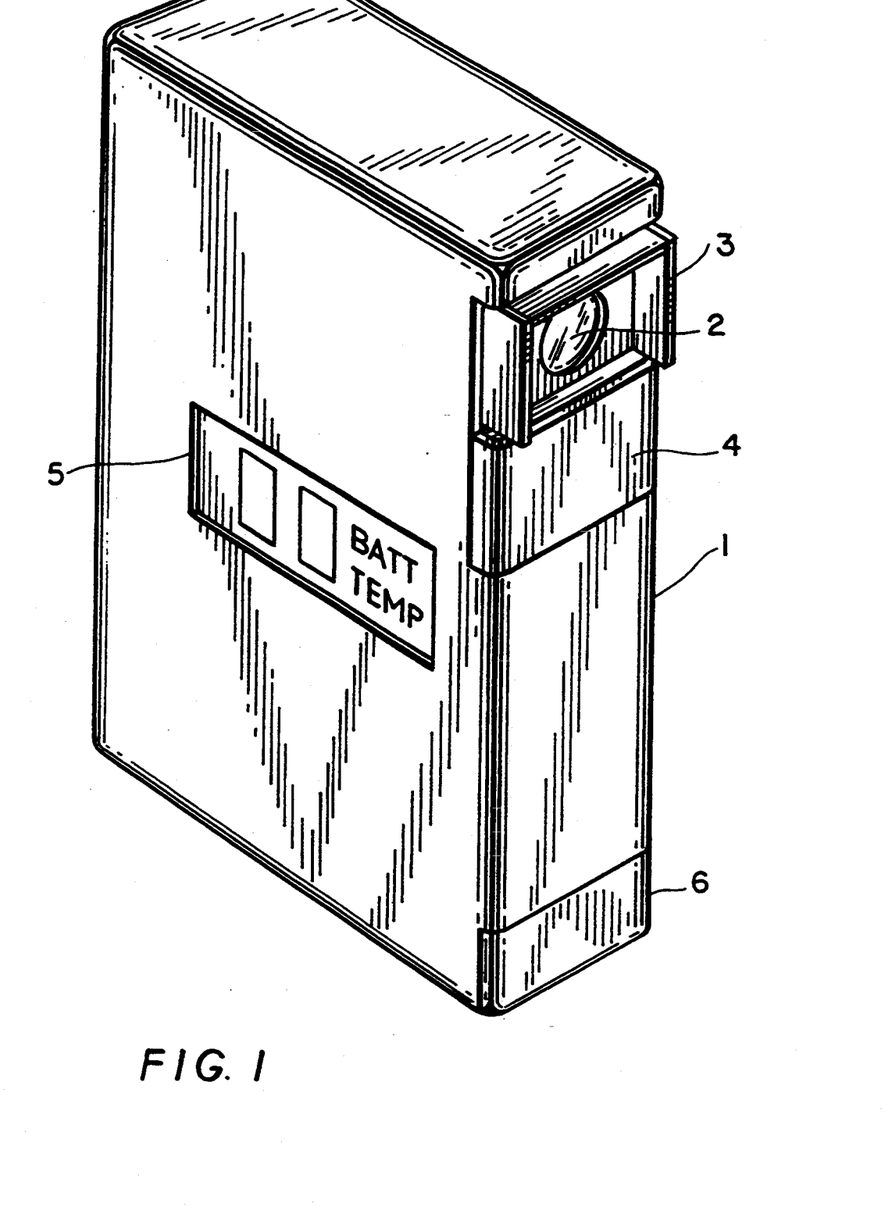
FIG. 1 is an external perspective view of a near-infrared instrument for the spectroscopic measurement of the aqueous humor of the eye for the purpose of determining blood glucose levels.

The spectrophotometer to make these measurements could take several configurations, such as a moderate sized laboratory instrument with remote fiber optic transmission of the energy to and/or from the eye or a small hand-held, portable, self-contained unit suitable for the user to carry easily in a pocket or purse. The latter preferred embodiment is illustrated in FIG. 1. The case 1 is preferably less than 30×80×130 mm (1.2×3.2×5.2 inches). The unit is used by looking into optical window 2 while holding the unit against the cheek to help steady it and establish the distance from the optics to the eyeball. Soft resilient ambient light shields 3 on each side unfold to lie between the unit and the face so as to substantially block ambient light. Preferably, an integral cover 4 is provided to protect the optical aperture and ambient light shields when the unit is stored. The inside of the cover 4 preferably comprises a reflecting means to redirect the source energy back into the detection means when the cover is closed, thereby providing a reference energy measurement that includes any optical window effects such as dirt or fingerprints. A display 5, preferably using an LCD or LED provides readout of the glucose value and instrument diagnostic and test information including battery status. A battery compartment 6 is provided at the opposite end of the instrument.

Figure 2:
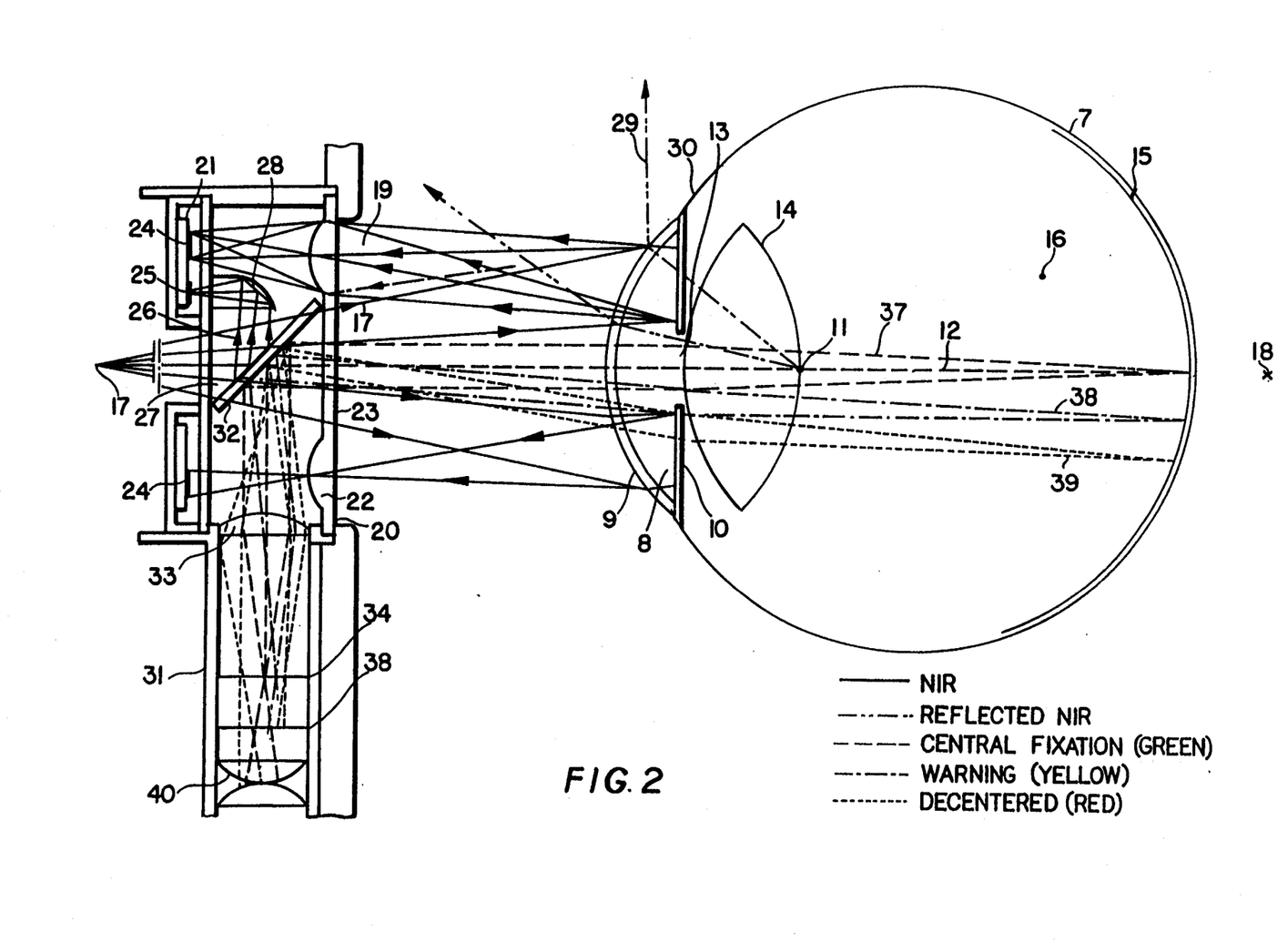
FIGS. 2, 2a, 2b are a detailed view, partially in cross section, of one preferred embodiment of the optical arrangement for illumination of the eye with spectrally encoded near-infrared energy, collection of the reflected energy, broadband detection means, and provision of the visible fixation point and other user information.
Figure 3:
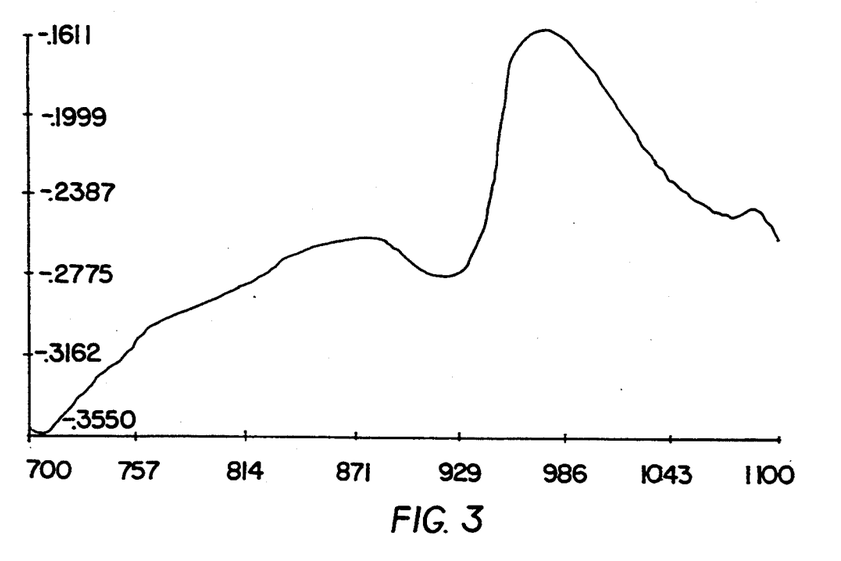
FIG. 3 is a near-infrared spectrum of the eye measured in the wavelength range from 700 to 1100 nanometers.
Figure 4:
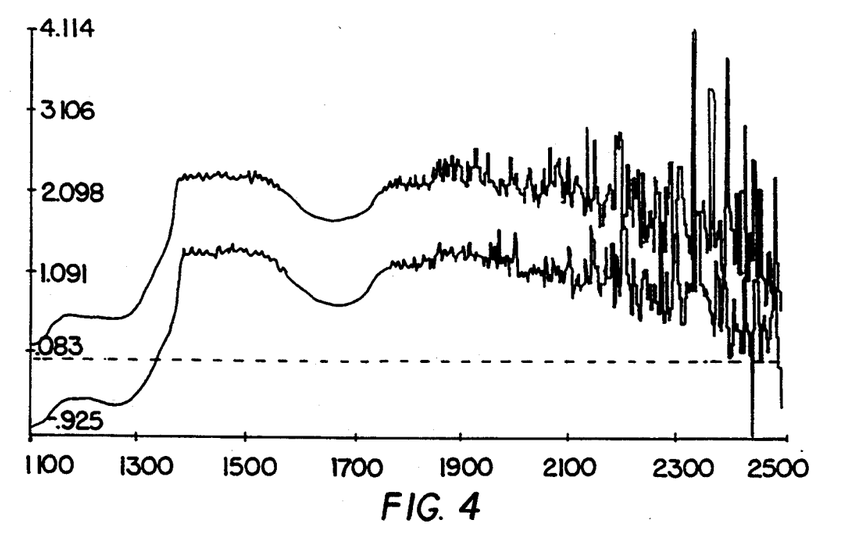
FIG. 4 shows two near-infrared spectra of the eye measured in the wavelength range from 1100 to 2500 nanometers.

The eye 7, which can be seen in cross section in FIG. 2, is a particularly useful site for measurements to determine blood glucose levels because it serves as a natural cuvette holding the aqueous humor 8 between the cornea 9, which serves as a window, and the iris 10. The approximately 3 mm depth of this chamber at its center is variable from person to person and the depth decreases away from the center. This depth is quite suitable for near-infrared spectroscopy in the near-infrared as is shown in FIG. 3, showing the spectrum of the eye with the strong water absorption band at 970 nanometers. Even the longer wavelength region shown in FIG. 4, in which the water peak centered at 1440 nanometers is saturated, shows the ability to measure below 1400 nanometers and even in the region between 1550 and 1750 nanometers. There are several glucose absorption bands within these usable regions of the near-infrared spectrum.

The aqueous humor is a clear transparent liquid composed largely of water with 7 to 8 g/l of NaCl, a level similar to that of blood plasma, but only 0.1 g/l of proteins compared to 60 to 70 g/l in blood plasma. NaCl does not absorb near-infrared light although it has a small effect on the spectrum of water. The low concentration of protein is advantageous in reducing its spectral interference, which has a major effect in plasma and blood. Other constituents include bicarbonates, lactic acid, ascorbic acid, and glucose. It is of great significance that the aqueous humor does not contain cells, which would cause scattering of the energy, nor hemoglobin, melanin, or other pigments which are strongly absorbing in the shorter wavelength near-infrared region and interfere with in vivo transcutaneous measurements of blood glucose. The aqueous humor is formed continuously, with about 1% of its total volume being produced and discharged each minute. Therefore, its glucose concentration can track that of the blood with a lag time constant sufficiently short (about 10 minutes) so that it is useful for blood glucose monitoring purposes.

Figure 2A:
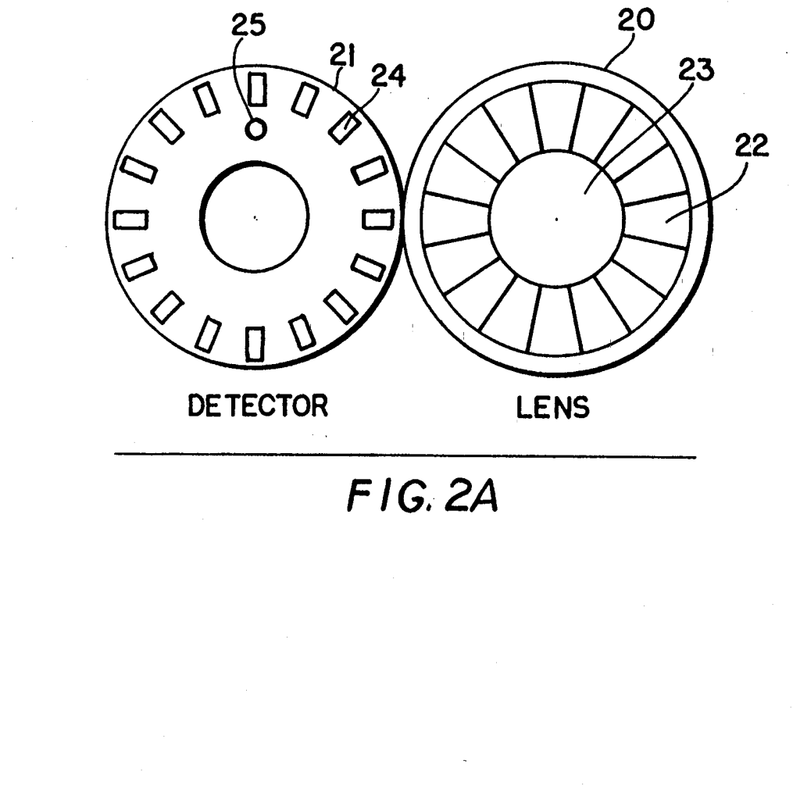
Figure 2B:
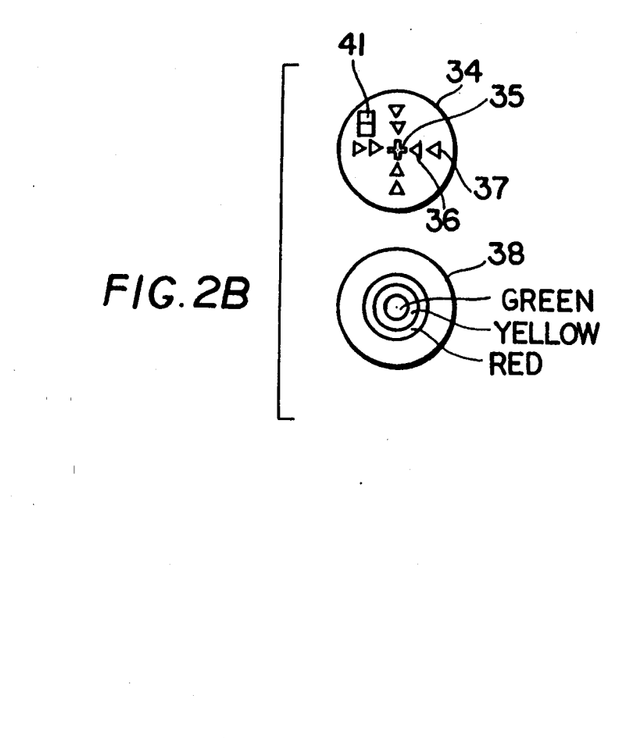

A first preferred optical arrangement for illuminating and measuring the reflected energy is shown in FIGS. 2, 2a and 2b. The eyeball 7 is approximately a 12 mm radius sphere, somewhat flattened on the anterior and posterior poles. The cornea 9 is a transparent membrane with a nearly spherical anterior surface of about 7.8 mm radius whose center of curvature 11 is about 5 mm forward of the center 12 of the eyeball. The thickness of the cornea at the anterior pole varies from 0.4 to 0.7 mm which increases towards the periphery yielding a posterior radius of about 6.5 mm. 90% of the corneal thickness is corneal stroma, formed mainly of collagen fibers and water. The iris 10 is a fairly flat disk about 12 mm in diameter pierced in its center with a variable circular pupil opening 13. The pupil diameter can vary from 1.5 mm to 10 mm. For example, the iris can dilate to 8 mm diameter in the dark and contract to 2 mm diameter in strong light. Moderate light typically produces a pupil diameter of about 4 mm. The amount of visible illumination reaching the eye is preferably controlled so that a pupil diameter of 2 to 4 mm results, causing at least 90% of the iris area to be available as a diffuse reflector of the near-infrared measuring illumination. The crystalline lens 14 lies behind the iris blocking the pupil opening. The space between the lens 14 and the retina 15 is then filled with the vitreous humor 16. The vitreous humor glucose level does not track blood glucose sufficiently well to be useful, however, the water absorption of vitreous humor allows almost no near-infrared energy to reach the retina, reflect, and escape to be included in the measurement. In addition, in the preferred embodiment, only the iris area is included in the measurement field with the pupil area blocked from view.

The optical power of the cornea is considered in this preferred optical arrangement. The near-infrared index of refraction of the cornea and aqueous humor is sufficiently close to the visible light values to use the known visible light optical power as the basis of this design. The object focal point 17 of the cornea is the origin point from which light will be collimated within the aqueous humor of the eye. This focal point is approximately 23.7 mm in front of the corneal apex. An f/2 beam of light from a small source area located at this position will spread to approximately 12 mm diameter at the corneal surface and then become collimated within the aqueous humor and fully illuminate the iris. The image focal point 18 of the cornea is approximately 31.5 mm behind the apex of the cornea. The reflected energy from the iris which is approximately parallel to the line from the reflecting point through the image focal point 18 of the cornea will exit the cornea approximately parallel to the optic axis and enter the detection aperture 19 where a segmented lens 20 piecewise reimages the iris on to the detection means 21. The molded segmented lens typically has sixteen lens segments 22, and a flat central region 23 through which the illuminating energy passes. It also serves as a sealed window for the unit.

The detection means 21 is preferably a photodiode detector of silicon or InGaAs comprising individual segments 24 matching the segments of the iris image produced by the segmented lens 20, although alternatively a ring detector may be used. The individual segments 24 are preferably electrically connected in parallel to sum the signal current. Preferably, an additional detector area 25 is provided for detection of the transmitted energy 26 to serve as a reference for the reflectance calculation. This energy from the source at 17 is reflected by mirror surfaces 27 and 28 onto detector area 25. This provides a continuous reference measurement to supplement and correct the reference measurement obtained from the inside of the cover.

The surface reflection of the cornea at normal incidence is approximately 2% which increases with the angle of incidence so that significant amounts of incident light may be reflected by the cornea. In the preferred embodiment, the optical geometry is arranged so that the specularly reflected near-infrared measurement energy is directed away from the measurement input considering the curved surface of the cornea as a mirror. For example, the corneal surface reflection of illuminating ray 17 becomes ray 29, which is directed completely away from the detection lens aperture 19. Ambient light might reflect from the cornea into the detection means so in the preferred embodiment, flexible shields 3 are provided to block the direct reflection of ambient light from the cornea or sclera 30 into the detection means. As described in more detail later, the near-infrared measurement energy is modulated so that it can be discriminated from any remaining ambient light.

A visible light projector 31 is provided to generate a central fixation point, other alignment cues, and additional information for the user. Mirror surface 32 comprises a dichroic coating which transmits near-infrared energy and reflects the visible light coaxially with the near-infrared source beam. Projection lens 33 projects the target pattern 34 as collimated beams so the target pattern is visually seen as if it were a great distance away. When the eye is properly located, light 37 from the central fixation-point target 36 passes through the pupil and is imaged on the retina so that the fixation point is visible to the user. If the eye is far from centered, the fixation-point light is blocked by the iris and it is therefore not visible.

Preferably, as an aid to the user, additional visual alignment cues 36 and 37 are provided and arranged so that they appear adjacent to and surround the central fixation point. In order to enhance the information provided the user, the optics are arranged so that the light from these cues is partially or completely blocked by the iris when the eye is centered. To accomplish this, the lens 33 also images the color separator 38 on the iris 10. Therefore, when the eye is centered, green light passes through the center of the pupil, yellow light is partially or completely blocked, depending on the pupil diameter, and red light is totally blocked by the iris. The optical color filtration and target geometry are such that the central fixation point 36 is green, the inner arrows 37 are yellow, and the outer arrows 38 are red. When the eye is centered, the user therefore sees a green fixation point, perhaps surrounded by dimmer yellow arrows of equal brightness and no red arrows. With decentering, one or two yellow arrows get brighter and then the green fixation point begins to disappear as one or two red arrows appear. The arrows always indicate the direction to the central fixation point. The light source 39 preferably comprises a number of different colored light emitting diodes whose energy is transferred to the appropriate areas of target 34 by the lenses 40. This provides individual control of the various target cues, which may be expanded to include one or more seven segment or other display elements 41.

Figure 5:
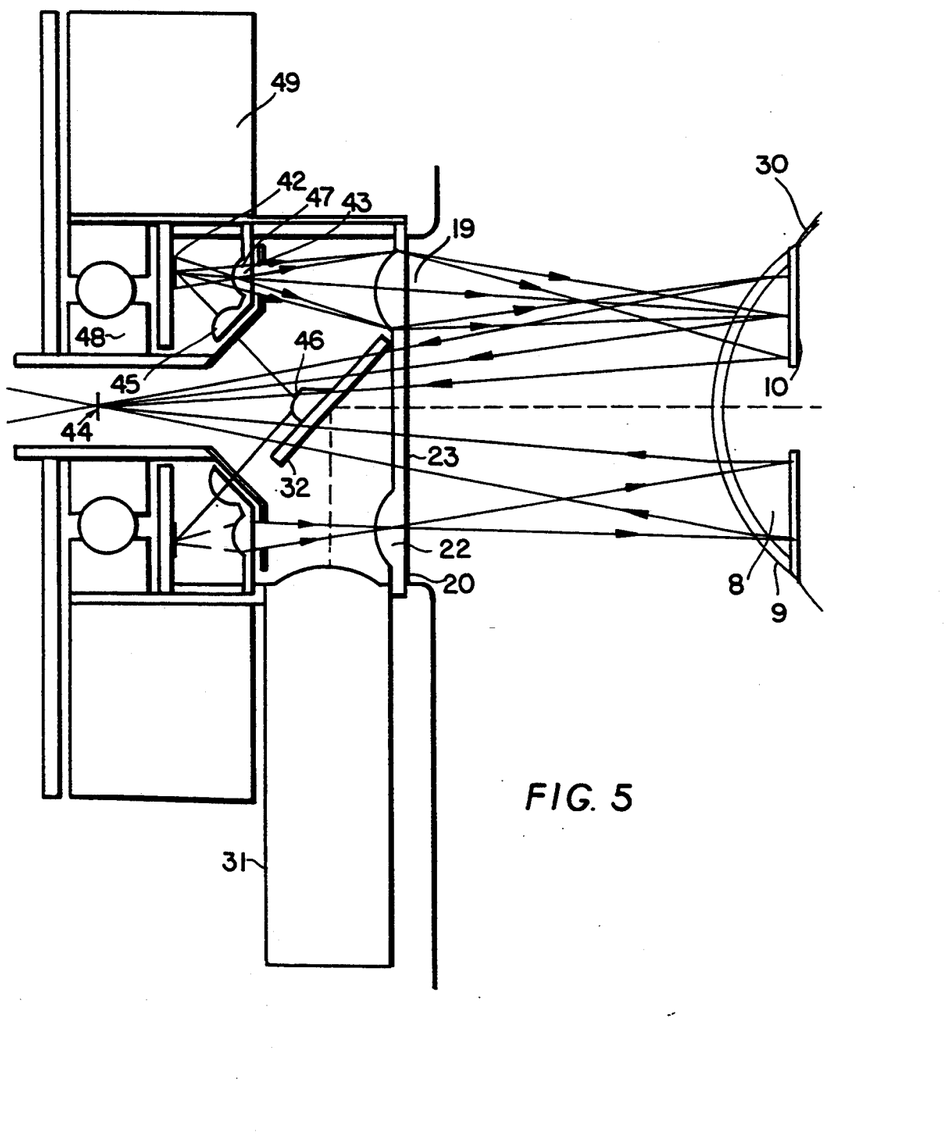
FIG. 5 is a detailed cross sectional view of a second preferred embodiment of the optical arrangement for illumination of the eye with broadband near-infrared energy, collection of the reflected energy, and spectrally selective detection means.

Conversely, in a second preferred arrangement shown in FIG. 5, the optical path is reversed with the detection aperture placed near the corneal focal point. Thus light reflected from the iris parallel to the optical axis will be focused into the detection means. This arrangement is preferred for spectrally selective detection means, such as a diode array spectrophotometer, which have limited optical throughput. Source 42 provides energy over the entire spectral bandwidth required, preferably using multiple light emitting diodes which can be electrically modulated at high rates and which have very long life. Alternatively, small tungsten filament lamps may be used, electrically modulated or mechanically modulated at a slower rate. The energy is collected by condensing optics 43, which comprise lenses or, alternatively, light pipes, and is then directed through the segmented lens/window 20 described above to illuminate the iris 10 of the eye. After being reflected back through the aqueous humor 8 and the cornea 9, the energy passes through the dichroic mirror 32 and enters the aperture 44 of the detection means. Some of the energy from the sources 42 is directed by lens 45 to segmented mirror 46 and thence to the detection aperture 44. Preferably, an electro-optical shutter, for example comprising a liquid crystal element, mounted in front of lenses 43 and 45, provides for alternately illuminating the eye via segmented lenses 43 and 20 or directing the source energy via lenses 45 and mirror 46 directly to the detection means or blocking the light completely, thus providing the ability to modulate the light source and to switch from reference to sample. Alternatively, as shown in FIG. 5, a mechanical chopper 47, mounted on bearings 48 and driven by printed circuit motor 49 is used to provide these functions. The visible light projector 31 described above is also used in this configuration.

In all these optical arrangements, the object is to obtain efficient transfer of energy from the source to the eye and from the eye to the detection means, while controlling the extent of the illumination and detection regions at the eye. Although the preferred arrangements described above incorporate lenses and mirrors, those skilled in the art will recognize that light pipes and fiber-optic elements may equally be used for some of these purposes. Also, the light emitting diodes described as the sources in the preferred implementation may be replaced by other types of sources, for example, small tungsten filament lamps.

In the first preferred embodiment of this invention, the light source defines the spectral separation of the various measurement wavelengths by sequentially turning on multiple sources of narrow band radiation or by modulating broad-band radiation as a function of wavelength. A preferred implementation of the former method utilizes light emitting diodes positioned with a diffraction grating so that the light of only a narrow wavelength band, typically 10 to 20 nanometers wide, from a particular diode will pass through the exit slit. Essentially, the diodes form multiple entrance slits to a spectrograph which has a single exit slit, the reverse of traditional operation. The wavelengths radiated from a light emitting diode of a given material composition typically cover a range of up to 200 nanometers thus many diodes may be formed on a single piece of material to provide energy at a multiplicity of wavelengths. Several diode substrates of different material composition may be used to cover the wavelength range of interest. An alternative known method employs narrow-band interference filters placed in front of individual diodes together with optical means to combine the energy from many such sources into a single beam. In either case, the diodes may be modulated electrically so that only one is turned on at a time or so that they operate simultaneously, each with a different modulation pattern which can be uniquely demodulated after detection, e.g. a pseudo-random code demodulated via the Hadamard transform.

In the alternative embodiment of this invention wherein the source is a broad-band source and the detection means provides the spectral selectivity, a preferred known configuration utilizes a diode-array spectrophotometer comprising an entrance slit, concave holographic grating, and diode-array detector. Improvements to such a diode-array spectrophotometer are described by Stark (U.S. Pat. No. 4,997,281). A diode-array detector can also be used in conjunction with an interference filter having a linear gradient in center wavelength.

It is also evident to those skilled in the art that a broad-band source may be modulated by an interferometer, as in Fourier transform spectroscopy, or by a electro-optical or moving mask, as in Hadamard transform spectroscopy, to encode wavelength information in the time domain. Also, a discrete wavelength band may be selected and scanned in center wavelength using, for example, an acousto-optical tuned filter. All that is required for the practice of this invention is one or more near-infrared sources, which provide energy at many wavelengths, near-infrared detection means, and means to distinguish information at each of said wavelengths after detection.

Figure 6:
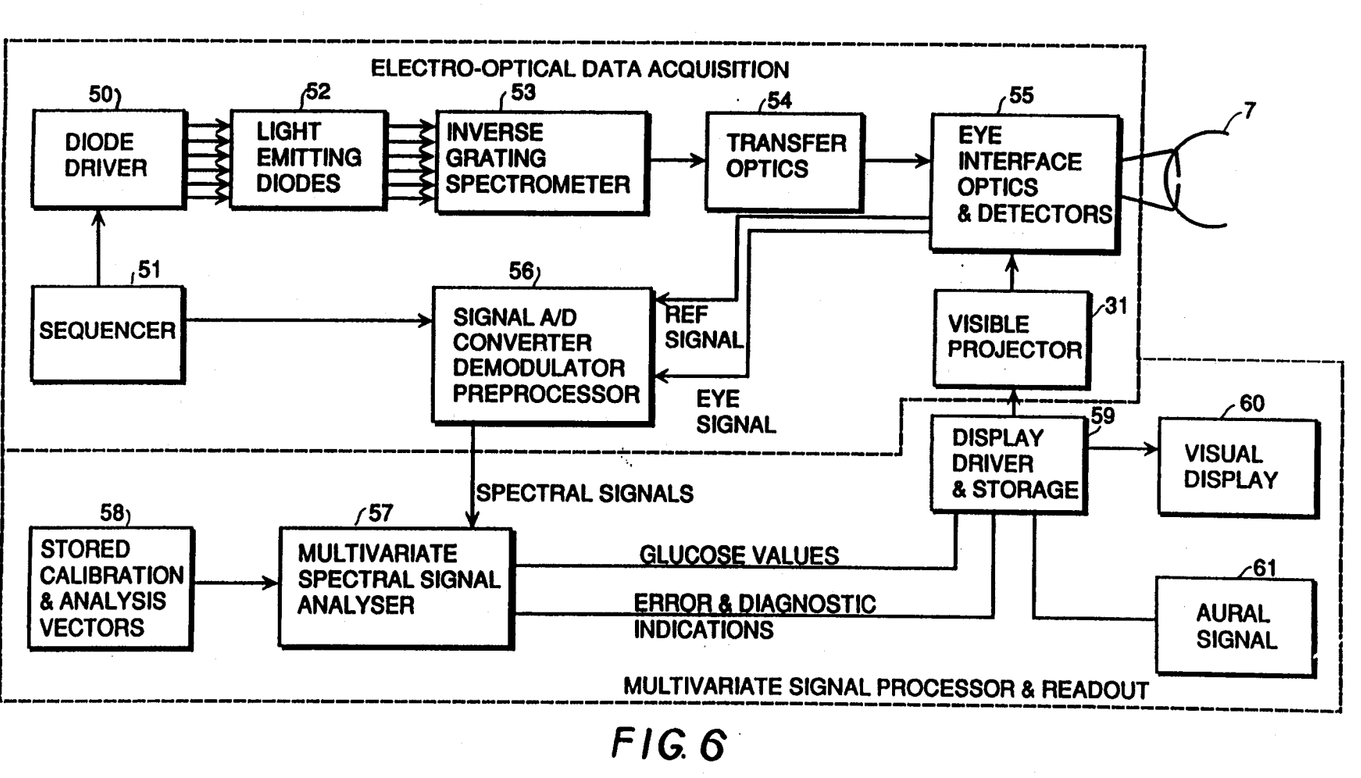
FIG. 6 is a block diagram of the first preferred embodiment of the invention comprising the electro-optical data acquisition subsystem and the multivariate signal processor and readout subsystem.

FIG. 6 is the block diagram of the first preferred embodiment of this invention using light emitting diodes 52 and a inverse grating spectrometer 53 as the source. The energy from the light emitting diodes is spectrally narrowed and combined in the inverse grating spectrometer 53 and then transferred by the transfer optics 54 from the exit slit of the spectrometer 53 to the source aperture 17 of the eye interface optics and detector module 55 described previously in reference to FIG. 2. The eye signal from detection elements 24 and the reference signal from detection element 25 are preamplified and sent to the signal A/D converter, demodulator, preprocessor 56.

The operation of the system is controlled by the sequencer 51 which provides the timing for the light emitting diode modulation to the diode driver electronics 50 and for the demodulation performed by the signal analog to digital converter, demodulator, and preprocessor 56. The modulation/demodulation signal waveform and processing are designed so that constant (DC) signals and signals at the powerline frequency and its harmonics are rejected while the modulated signals from the light emitting diodes are demodulated and utilized. The preprocessor standardizes the signals based on measured and stored instrument characteristics and the measured reference signal data. The resultant spectral signals are expressed as the corrected ratio of the eye and reference signals, linearized with respect to concentration, e.g. by taking the log of the ratio to generate absorbance. Due to the variable length of different paths through the anterior chamber of the eye, more complex empirically derived linearization functions are preferred. In addition, other known preprocessing techniques, such as multiplicative signal correction, derivatives, and derivative ratios are utilized to minimize the effects of undesired signal variables.

The spectral signals are processed in the multivariate spectral signal analyzer 57 using the stored calibration and signal analysis vectors 58. In the analyzer 57, the signals are classified as to their similarity to the signals used in calibration using known multivariate classification techniques. Inaccurate signals are rejected and a diagnostic indication provided to the user via the display driver and storage 59, the previously described display in the visible projector 31, and the aural signal 61. Sufficiently accurate signals are further processed using multivariate estimation techniques such as multiple linear regression (MLR), principle components regression (PCR), and partial least squares regression (PLS), as described by Martens and Naes. Additional tests of the validity of the glucose estimates are performed during this spectral modeling process. Valid glucose results are averaged and sent to the display driver and storage 59, where the result are stored for later recall as desired by the user, and thence to the visual display 60. Visual and aural indications are provided if errors occur and for instrument diagnostic purposes.

Figure 7:
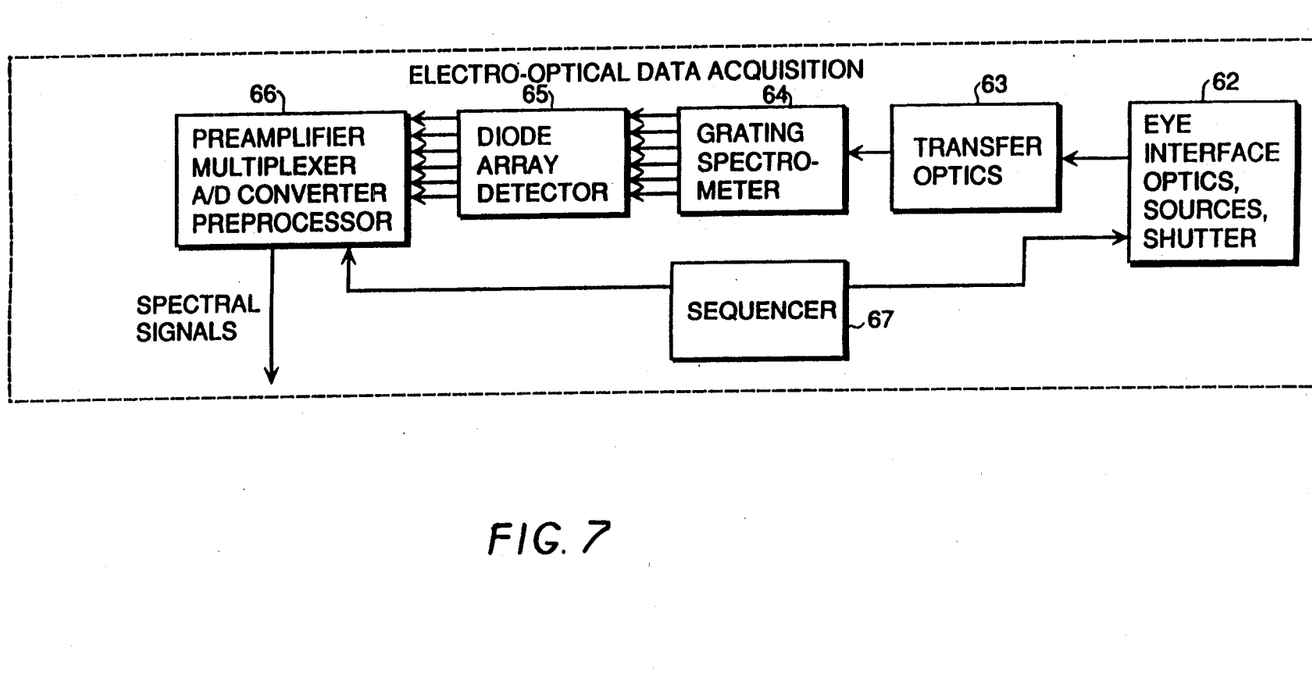
FIG. 7 is a block diagram of the electro-optical data acquisition subsystem of the second preferred embodiment of the invention.

FIG. 7 is the block diagram of the alternative electro-optical data acquisition subsystem using a diode array spectrometer. The broad-band light source is within the eye interface optics, sources, and shutter module 62 described previously with respect to FIG. 5. The light reflected from the eye exits this module via the aperture 44 and is transferred to the entrance slit of the grating spectrometer 64 by the transfer optics 63. The diode array detector 65 outputs a signal for each wavelength band being measured. The preamplifier-multiplexer- A/D converter-preprocessor 66 amplifies and combines the individual diode signals into an A/D converter. Sequencer 67 controls the modulation of the light sources and shutter and provides timing to the preprocessor for demodulation of the reference and eye signals. From this point on, the operation of the preprocessor is the same as described above and this embodiment provides the same type of spectral signals to the multivariate signal processor and readout.

While the foregoing description and drawings represent the preferred embodiments of the present invention, it will be obvious to those skilled in the art that various changes and modifications may be made therein without departing from the true spirit and scope of the present invention.

What is claimed is:

1. A method of determining non-invasively and in vivo the concentration of blood glucose, said method comprising the steps of:
   a) irradiating in vivo and non-invasively the eye with near-infrared energy having at least several wavelengths, the energy being reflected from at least one structure within the anterior portion of the eye and reemerging after having undergone differential absorption at least within the aqueous humor of at least some of said wavelengths characteristic of glucose and other constituents of the eye and their respective unknown concentrations;
   b) measuring the spectral intensity of the near-infrared energy reemerging from the eye and producing electrical signals representative of said measured intensity; and
   c) calculating the unknown concentration of blood glucose from variations of said measured intensity signals.

2. The method of claim 1 wherein said calculating step includes processing said measured intensity signals using multivariate modeling and calibration techniques.

3. The method of claim 1 wherein said near-infrared energy is broad band and optically encoded with respect to wavelength spectral information in a manner such as to be decodable after detection.

4. The method of claim 1 wherein said irradiating step includes the step of directing the near-infrared energy so that the specular reflection of the electromagnetic energy from the curved anterior surfaces of the cornea and sclera is not measured.

5. The method of claim 1 wherein said irradiating step includes the further step of substantially blocking extraneous light from the surrounding environment so it is not measured.

6. Apparatus for determining non-invasively and in vivo the concentration of blood glucose comprising:
   means for irradiating in vivo and non-invasively an eye with near-infrared energy having at least several wavelengths, said energy being reflected from at least one structure within the anterior portion of eye and reemerging after having undergone differential absorption within the aqueous humor of at least some of said wavelengths characteristic of glucose and other constituents of the eye in relation to respective concentrations;
   means for measuring the spectral intensity of the near-infrared energy reemerging from the eye and producing electrical signals representative of said measured intensity; and
   means for calculating the concentration of blood glucose from variations of said measured spectral intensity signals.

7. The apparatus of claim 6 wherein said means for calculating includes means for processing said measured spectral intensity signals using multivariate modeling and calibration techniques.

8. The apparatus of claim 7 wherein said signals are classified as being appropriate for use and analyzed if appropriate to determine whether they conform to an applicable multivariate calibration model.

9. The apparatus of claim 6 wherein said irradiating means provides broad band infrared energy which is spectrally encoded in narrow wavelength bands, said measuring means operating to collect the reflected energy and convert it to a composite electrical signal representative of the energy at all wavelengths simultaneously; means being provided for decoding the composite electrical signals relating to the reflected energy at each of the multiplicity of narrow wavelength bands which comprise the broad band energy to the eye, said calculating means being responsive to said coded signals.

10. The apparatus of claim 9 wherein an interferometer is provided for spectral encoding of said near-infrared energy and said decoding means is a Fourier transform decoder.

11. The apparatus of claim 9 wherein a time-variable encoding mask placed in a dispersed spectral image is provided for spectral encoding of said near-infrared energy and said decoding means is a time sequence decoder.

12. The apparatus of claim 9 wherein said encoding means includes electrical modulation of multiple discrete sources, said decoding means being capable of separating the measured signal based on the modulation of the reflected energy.

13. The apparatus of claim 12 wherein said source are light emitting diodes.

14. The apparatus of claim 6 wherein said irradiating means and measuring means are configured and positioned to direct the specular reflection of the electromagnetic energy from the curved anterior surfaces of the cornea away from the detection means to prevent spectroscopic errors associated with the detection of energy which has not undergone absorption.

15. The apparatus of claim 6 wherein said measuring means is configured and positioned so that extraneous energy from the surrounding environment is substantially blocked from reaching said detection means.

16. The apparatus of claim 6 wherein said means for calculating includes means for processing said measured intensity signals by univariate modeling and calibration techniques.

17. The apparatus of claim 6 further including means for rapidly repeating the entire measurement sequence at a sufficiently high rate so that movement of the apparatus will not cause significant errors.

18. The apparatus of claim 6 further including means for providing a signal to the user to indicate that the signals obtained are suitable for processing.

19. The apparatus of claim 6 further including means for providing a signal to the user that sufficient acceptable signals have been accumulated, the glucose value is computed and that the measurement is complete.

20. Apparatus for determining non-invasively and in vivo the concentration of blood glucose comprising:

means for irradiating in vivo and non-invasively an eye with near-infrared energy having at least several wavelengths, said energy entering the eye and being reflected from at least one structure within the anterior portion of the eye and reemerging after having undergone differential absorption within the aqueous humor of at least some of said wavelengths characteristic of glucose and other constituents of the eye in relation to respective concentrations, said irradiating energy being modulated by modulating signals provided by modulating means;

means for measuring the spectral intensity of the near-infrared energy reemerging from the eye and producing electrical signals representative of said measured intensity;

means for calculating the concentration of blood glucose from variations of said measured spectral intensity signals; and wherein said measuring means and calculating means are responsive only to energy modulated by said modulating signals while discriminating against interference signals.

21. Apparatus for determining non-invasively and in-vivo the unknown value of blood glucose comprising:

means for irradiating in vivo and non-invasively an eye with near-infrared energy having at least several wavelengths, said energy being reflected from at least one structure within the anterior portion of the eye and reemerging after having undergone differential absorption of at least some of said wavelengths characteristic of glucose and other constituents of the eye and their respective unknown concentration;

means for measuring the spectral intensity of the near-infrared energy reemerging from the eye and producing electrical signals representative of said measured intensity; and means for calculating the unknown concentration of blood glucose from variations of said measured spectral intensity signals; and including fixation means for producing visible light so directed as to provide a fixation point for a user, thereby aiding the user to maintain the proper location and orientation of the irradiating means and measuring means.

22. The apparatus of claim 21 wherein said fixation means provides visible light at an intensity to cause the pupil to contract thereby maximizing the reflecting area of the iris.

23. The apparatus of claim 21 wherein said fixation means provides a plurality of visible light sources in a pattern indicative of positioning errors and their direction, the light from which being at least partially blocked by the iris when the apparatus is correctly positioned.

24. A method of determining non-invasively and in vivo the concentration of blood glucose, said method comprising the steps of:

a) irradiating in vivo and non-invasively the eye with near-infrared energy having at least several wavelengths, said energy entering the eye and being reflected from at least one structure within the anterior portion of the eye and reemerging after having undergone differential absorption at least within the aqueous humor of at least some of said wavelengths characteristic of glucose and other constituents of the eye and their respective unknown concentrations;

b) measuring the spectral intensity of the near-infrared energy reemerging from the eye and producing electrical signals representative of said measured intensity, said measuring step including measuring the near-infrared energy reflected from the iris and reemerging from the eye; and c) calculating the unknown concentration of blood glucose from variations of said measured intensity signals.

25. Apparatus for determining non-invasively and in vivo the concentration of blood glucose comprising:

means for irradiating in vivo and non-invasively an eye with near-infrared energy having at least several wavelengths, said energy being reflected from at least one structure within the anterior portion of the eye and reemerging after having undergone differential absorption within the aqueous humor of at least some of said wavelengths characteristic of glucose and other constituents of the eye in relation to respective concentrations;

means for measuring the spectral intensity of the near-infrared energy reemerging from the eye and producing electrical signals representative of said measured intensity, said measuring means operating to measure the spectral intensity of the near-infrared energy reflected from the iris and reemerging from the eye; and means for calculating the concentration of blood glucose from variations of said measured spectral intensity signals.

26. A method of determining non-invasively and in vivo the concentration of blood glucose, said method comprising the steps of:

a) irradiating in vivo and non-invasively the eye with near-infrared energy having at least several wavelengths, the energy being reflected from at least one structure within the anterior portion of the eye and reemerging after having undergone differential absorption at least within the aqueous humor of at least some of said wavelengths characteristic of glucose and other constituents of the eye and their respective unknown concentrations.;

b) measuring the spectral intensity of the near-infrared energy reemerging from the eye and producing electrical signals representative of said measured intensity; and c) calculating the concentration of blood glucose from variations of said measured intensity signals, and further including the step of providing a visible light fixation point for a user, thereby aiding the user to maintain the proper location and orientation of the irradiating means and measuring means.

27. The method of claim 26 further comprising the step of illuminating the eye at an intensity to cause the pupil to contract thereby maximizing the reflecting area of the iris.

28. The method of claim 26 further comprising the step of providing a visible light pattern indicative of positioning errors and their direction, the light from which being at least partially blocked by the iris when the apparatus is correctly positioned.

29. A method of determining non-invasively and in vivo the concentration of glucose in the aqueous humor of the eye, said method comprising the steps of:

a) irradiating in vivo and non-invasively the eye with near-infrared energy having at least several wavelengths, the energy being reflected from at least one structure within the anterior portion of the eye and reemerging after having undergone differential absorption within the aqueous humor of at least some of said wavelengths characteristic of glucose and other constituents of the eye and their respective unknown concentrations;

b) measuring the spectral intensity of the near-infrared energy reemerging from the eye and producing electrical signals representative of said measured intensity; and c) calculating the unknown concentration of glucose in the aqueous humor of the eye from variations of said measured intensity signals.

30. The method of claim 29 further including the step of deriving the concentration of blood glucose from the calculated concentration of glucose in the aqueous humor of the eye.

* * * * *